US009956000B2

(12) United States Patent
Gardanier et al.

(10) Patent No.: US 9,956,000 B2
(45) Date of Patent: May 1, 2018

(54) INSERTION TOOL FOR IMPLANTING A PADDLE LEAD AND METHODS AND SYSTEMS UTILIZING THE TOOL

(71) Applicant: Boston Scientific Neuromodulation Corporation, Valencia, CA (US)

(72) Inventors: Lauren Gardanier, Saratoga, CA (US); Joshua Dale Howard, Winnetka, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 78 days.

(21) Appl. No.: 14/982,669

(22) Filed: Dec. 29, 2015

(65) Prior Publication Data
US 2016/0199096 A1 Jul. 14, 2016

Related U.S. Application Data

(60) Provisional application No. 62/102,999, filed on Jan. 13, 2015.

(51) Int. Cl.
*A61N 1/05* (2006.01)
*A61B 17/34* (2006.01)

(52) U.S. Cl.
CPC ........ *A61B 17/3468* (2013.01); *A61N 1/0553* (2013.01); *A61N 1/0558* (2013.01)

(58) Field of Classification Search
CPC ............... A61N 1/0553; A61N 1/0588; A61N 2001/0578; A61N 1/056; A61N 1/0587; A61B 17/3468; A61B 2019/208
USPC ........................................................ 606/129
See application file for complete search history.

(56) References Cited

U.S. PATENT DOCUMENTS

| 3,646,940 | A | 3/1972 | Timm et al. |
| 3,724,467 | A | 4/1973 | Avery et al. |
| 4,141,365 | A | 2/1979 | Fischell et al. |
| 4,166,469 | A | 9/1979 | Littleford |
| 4,270,549 | A | 6/1981 | Heilman |

(Continued)

FOREIGN PATENT DOCUMENTS

| EP | 1048270 | 11/2000 |
| WO | 2014/099412 | 6/2014 |

OTHER PUBLICATIONS

International Search Report and Written Opinion for PCT Application No. PCT/US2015/067844 dated Apr. 18, 2016.

*Primary Examiner* — Kathleen Holwerda
(74) *Attorney, Agent, or Firm* — Lowe Graham Jones PLLC; Bruce E. Black (57) ABSTRACT

A paddle lead insertion tool includes an insertion tool body having a delivery end portion, a delivery end portion, and a slider slit; a slider partially disposed within the slider slit; extenders coupled to the slider and extending to the delivery end portion to receive a paddle body between or upon the extenders; and a center push piece coupled to the slider and disposed between the extenders to push against a proximal end of the paddle body. The slider moves between an insertion position and a delivery position. The insertion tool extends the extenders and center push piece when the slider moves from the insertion position to the delivery position to extend a paddle body received by the insertion tool. The insertion tool retracts the extenders without retracting the center push piece when the slider moves from the delivery position towards the insertion position.

20 Claims, 8 Drawing Sheets

(56) References Cited

U.S. PATENT DOCUMENTS

| | | |
|---|---|---|
| 4,291,707 A | 9/1981 | Heilman et al. |
| 4,379,462 A | 4/1983 | Borkan et al. |
| 4,512,351 A | 4/1985 | Pohndorf |
| 4,765,341 A | 8/1988 | Mower et al. |
| 4,989,617 A | 2/1991 | Memberg et al. |
| 5,143,067 A | 9/1992 | Rise et al. |
| 5,249,574 A | 10/1993 | Bush et al. |
| 5,282,468 A | 2/1994 | Klepinski |
| 5,391,200 A | 2/1995 | KenKnight et al. |
| 5,397,342 A | 3/1995 | Heil, Jr. et al. |
| 5,417,719 A | 5/1995 | Hull et al. |
| 5,618,287 A | 4/1997 | Fogarty et al. |
| 5,643,330 A | 7/1997 | Holsheimer et al. |
| 5,733,322 A | 3/1998 | Starkebaum |
| 6,027,456 A | 2/2000 | Feler et al. |
| 6,181,969 B1 | 1/2001 | Gord |
| 6,205,361 B1 | 3/2001 | Kuzma et al. |
| 6,249,707 B1 | 6/2001 | Kohnen et al. |
| 6,309,401 B1 | 10/2001 | Redko et al. |
| 6,319,241 B1 | 11/2001 | King et al. |
| 6,415,187 B1 | 7/2002 | Kuzma et al. |
| 6,516,227 B1 | 2/2003 | Meadows et al. |
| 6,522,932 B1 | 2/2003 | Kuzma et al. |
| 6,553,264 B2 | 4/2003 | Redko et al. |
| 6,605,094 B1 | 8/2003 | Mann et al. |
| 6,609,029 B1 | 8/2003 | Mann et al. |
| 6,609,032 B1 | 8/2003 | Woods et al. |
| 6,714,822 B2 | 3/2004 | King et al. |
| 6,741,892 B1 | 8/2004 | Meadows et al. |
| 6,895,283 B2 | 5/2005 | Erickson et al. |
| 7,050,858 B1 * | 5/2006 | Kuzma .............. A61B 17/3403 606/129 |
| 7,244,150 B1 | 7/2007 | Brase et al. |
| 7,343,202 B2 * | 3/2008 | Mrva .................. A61N 1/0524 607/116 |
| 7,672,734 B2 | 3/2010 | Anderson et al. |
| 7,761,165 B1 | 7/2010 | He et al. |
| 7,949,395 B2 | 5/2011 | Kuzma |
| 8,244,459 B2 | 7/2012 | Pianca et al. |
| 2003/0171758 A1 * | 9/2003 | Gibson .............. A61B 17/3468 606/129 |
| 2004/0059392 A1 | 3/2004 | Parramon et al. |
| 2005/0070919 A1 * | 3/2005 | Lieberman ........... A61N 1/0553 606/108 |
| 2005/0165465 A1 | 7/2005 | Pianca et al. |
| 2007/0150036 A1 | 6/2007 | Anderson |
| 2007/0219595 A1 | 9/2007 | He |
| 2007/0239243 A1 | 10/2007 | Moffitt et al. |
| 2008/0071320 A1 | 3/2008 | Brase |
| 2008/0306335 A1 * | 12/2008 | Lau .................. A61B 17/00008 600/106 |
| 2010/0179562 A1 | 7/2010 | Linker et al. |
| 2011/0319909 A1 | 12/2011 | Thenuwara et al. |
| 2012/0271315 A1 | 10/2012 | Pianca et al. |
| 2012/0271316 A1 | 10/2012 | Pianca et al. |
| 2012/0283744 A1 | 11/2012 | Slavin |
| 2013/0066331 A1 | 3/2013 | Chitre et al. |
| 2013/0268041 A1 | 10/2013 | Schulte et al. |
| 2013/0289685 A1 | 10/2013 | Browne et al. |
| 2015/0151114 A1 * | 6/2015 | Black .................. A61N 1/0553 607/117 |
| 2015/0258331 A1 * | 9/2015 | Dadd ................. A61B 17/3468 606/129 |
| 2016/0166828 A1 * | 6/2016 | Yu ........................ A61N 1/0553 607/116 |

\* cited by examiner

INSERTION TOOL FOR IMPLANTING A PADDLE LEAD AND METHODS AND SYSTEMS UTILIZING THE TOOL

CROSS-REFERENCE TO RELATED APPLICATIONS

This application claims the benefit under 35 U.S.C. § 119(e) of U.S. Provisional Patent Application Ser. No. 62/102,999, filed Jan. 13, 2015, which is incorporated herein by reference.

FIELD

The present invention is directed to the area of implantable electrical stimulation systems and methods of making and using the systems. The present invention is also directed to an insertion tool suitable for facilitating implantation of paddle bodies of electrical stimulation leads, as well as methods of making and using the insertion tool, paddle bodies, leads, and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is a paddle lead insertion tool including an insertion tool body having a delivery end portion, a delivery end portion, and a slider slit; a slider having a portion disposed within the slider slit; extenders coupled to the slider and extending to the delivery end portion to receive a paddle body of a paddle lead between or upon the extenders; and a center push piece coupled to the slider and disposed between the extenders to push against a proximal end of the paddle body of the paddle lead. The slider moves between an insertion position and a delivery position. The insertion tool extends the extenders and center push piece when the slider moves from the insertion position to the delivery position to extend a paddle body received by the insertion tool. The insertion tool retracts the extenders without retracting the center push piece when the slider moves from the delivery position towards the insertion position.

In at least some embodiments, the extenders each include a vertical or curved rail configured and arranged to be disposed adjacent sides of the paddle body. In at least some embodiments, the extenders each include a horizontal platform configured and arranged to be at least partially disposed beneath a portion of the paddle body. In at least some embodiments, the insertion tool also includes a crosspiece coupling ends of the extenders.

In at least some embodiments, the insertion tool also includes cabling coupled to the slider and to distal end portions of the extenders to cooperate with the slider and the extenders for steering the paddle body. In at least some embodiments, the slider includes a rotatable slider wheel coupled to the cabling to rotate and pull the distal end portion of one of the extenders for steering the paddle body.

In at least some embodiments, the slider moves along a first direction between the insertion position and the delivery position and the delivery end portion of the insertion tool body includes a curved delivery ramp to deliver a paddle body received by the insertion tool at an angle, defined between the paddle body and the first direction, in a range of 80 to 100 degrees. In at least some embodiments, the angle is in a range from 85 to 95 degrees.

Another embodiment is a method of implanting a paddle lead that includes disposing a paddle body of the paddle lead between or upon the extenders of any of the insertion tools described above; inserting the insertion tool and paddle body into the patient; advancing the slider to the delivery position to extend the extenders, the center push piece, and the paddle body toward an implantation site within the patient; retracting the slider to retract the extenders without retracting the center push piece to deliver the paddle body at the implantation site; and removing the insertion tool leaving the paddle body at the implantation site.

Yet another embodiment is a paddle lead insertion tool including an insertion tool body having a delivery end portion, a delivery end portion, and a slider slit; a slider having a portion disposed within the slider slit to move along a first direction between an insertion position and a delivery position and the delivery end portion of the insertion tool body includes a curved delivery ramp to deliver a paddle body received by the insertion tool at an angle, defined between the paddle body and the first direction, in a range of 70 to 110 degrees; and extenders coupled to the slider and extending to the delivery end portion to receive a paddle body of a paddle lead between or upon the extenders. The slider moves between an insertion position and a delivery position. The insertion tool extends the extenders when the slider moves from the insertion position to the delivery position to extend a paddle body received by the insertion tool. The insertion tool retracts the extenders when the slider moves from the delivery position towards the insertion position.

In at least some embodiments, the insertion tool also includes a center push piece coupled to the slider and disposed between the extenders to push against a proximal end of the paddle body of the paddle lead, where the insertion tool extends the extenders and center push piece when the slider moves from the insertion position to the delivery position to extend a paddle body received by the insertion tool and the insertion tool retracts the extenders without retracting the center push piece when the slider moves from the delivery position towards the insertion position.

In at least some embodiments, the angle is in a range from 80 to 100 degrees. In at least some embodiments, the angle is in a range from 85 to 95 degrees. In at least some embodiments, the insertion tool also includes cabling coupled to the slider and to distal end portions of the extenders and configured and arranged to cooperate with the slider and the extenders for steering the paddle body. In at least some embodiments, the slider includes a rotatable slider wheel coupled to the cabling to rotate and pull the distal end portion of one of the extenders for steering the paddle body.

In at least some embodiments, the extenders each include a vertical or curved rail configured and arranged to be disposed adjacent sides of the paddle body. In at least some embodiments, the extenders each include a horizontal platform configured and arranged to be at least partially disposed beneath a portion of the paddle body.

A further embodiment is a method of implanting a paddle lead that includes disposing a paddle body of the paddle lead between or upon the extenders of any one of the insertion tools described above; inserting the insertion tool and paddle body into the patient; advancing the slider to the delivery position to extend the extenders and the paddle body toward an implantation site within the patient; retracting the slider to retract the extenders to deliver the paddle body at the implantation site; and removing the insertion tool leaving the paddle body at the implantation site.

Another embodiment is an insertion kit that includes any of the insertion tools described above; and a paddle lead having a paddle body, at least one lead body extending from the paddle body, electrodes disposed on the paddle body, and terminals disposed along the at least one lead body and electrically coupled to the electrodes. The insertion kit optionally includes a control module coupleable to the lead.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to an insertion tool suitable for facilitating implantation of paddle bodies of electrical stimulation leads, as well as methods of making and using the insertion tool, paddle bodies, leads, and electrical stimulation systems.

Suitable implantable electrical stimulation systems include, but are not limited to, at least one lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; and 7,761,165; and U.S. Patent Applications Publication Nos. 2005/0165465, 2007/0150036; 2007/0219595; 2007/0239243; and 2008/0071320, all of which are incorporated by reference.

Figure 1:
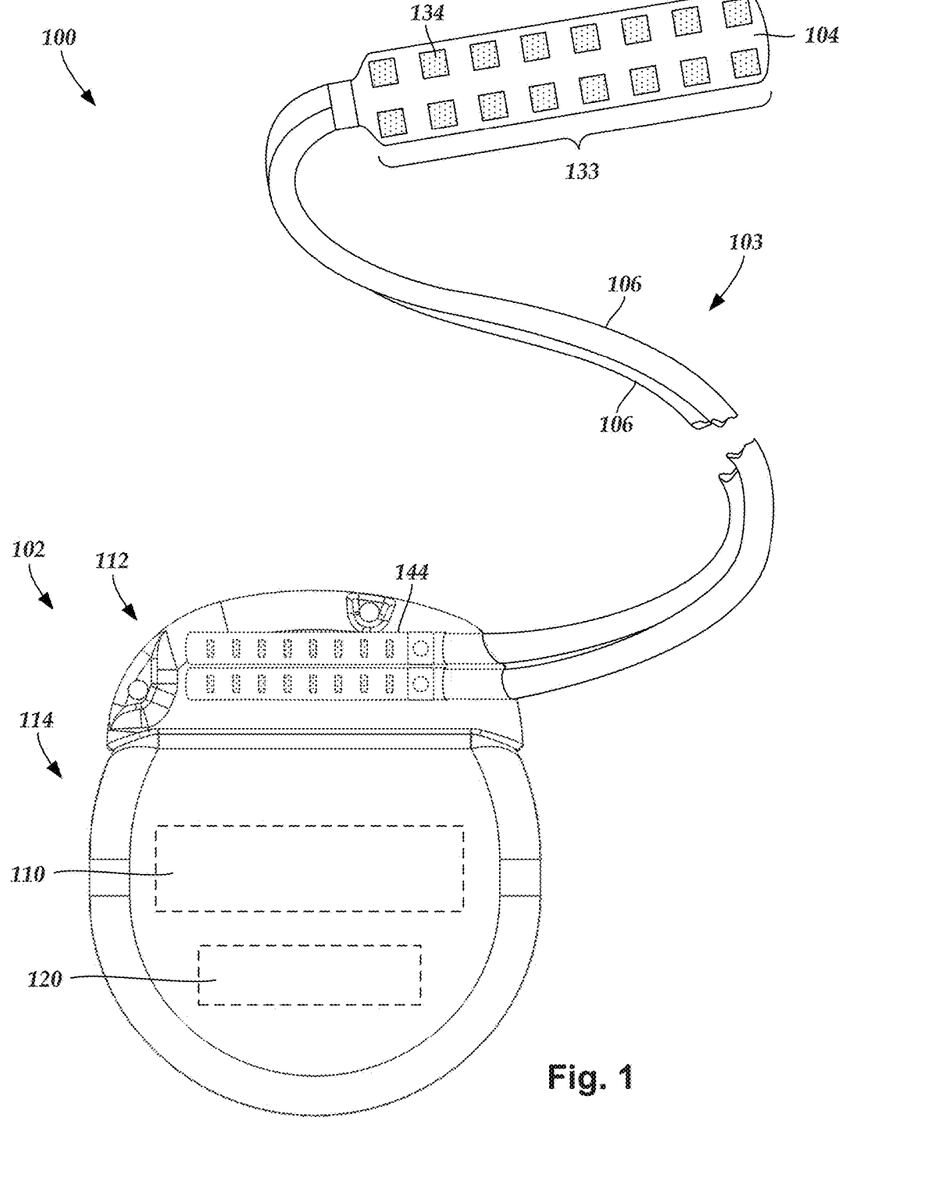
FIG. 1 is a schematic side view of one embodiment of an electrical stimulation system that includes a lead electrically coupled to a control module, according to the invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes a paddle body 104 and one or more lead bodies 106. In FIG. 1, the lead 103 is shown having two lead bodies 106. It will be understood that the lead 103 can include any suitable number of lead bodies including, for example, one, two, three, four, five, six, seven, eight or more lead bodies 106. An array of electrodes 133, such as electrode 134, is disposed on the paddle body 104, and an array of terminals (e.g., 210 in FIG. 2A-2B) is disposed along each of the one or more lead bodies 106.

The lead 103 can be coupled to the control module 102 in any suitable manner. In FIG. 1, the lead 103 is shown coupling directly to the control module 102. In at least some other embodiments, the lead 103 couples to the control module 102 via one or more intermediate devices. For example, in at least some embodiments one or more lead extensions 224 (see e.g., FIG. 2B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

The control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including the paddle body 104, the one or more of the lead bodies 106, and the control module 102, are typically implanted into the body of a patient. The electrical stimulation system can be used for a variety of applications including, but not limited to neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium.

Any suitable number of electrodes 134 can be disposed on the paddle body including, for example, four, five, six, seven, eight, nine, ten, eleven, twelve, fourteen, sixteen, twenty-four, thirty-two, or more electrodes 134. The electrodes 134 can be disposed on the paddle body 104 in any suitable arrangement. In FIG. 1, the electrodes 134 are arranged into two columns, where each column has eight electrodes 134.

The electrodes of the paddle body 104 are typically disposed in, or separated by, a non-conductive, biocompatible material such as, for example, silicone, polyurethane, polyetheretherketone ("PEEK"), epoxy, and the like or combinations thereof. The paddle body 104 and the one or more lead bodies 106 may be formed in the desired shape by any process including, for example, molding (including injection molding), casting, and the like. The non-conductive material typically extends from the paddle body 104 to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Figure 2A:
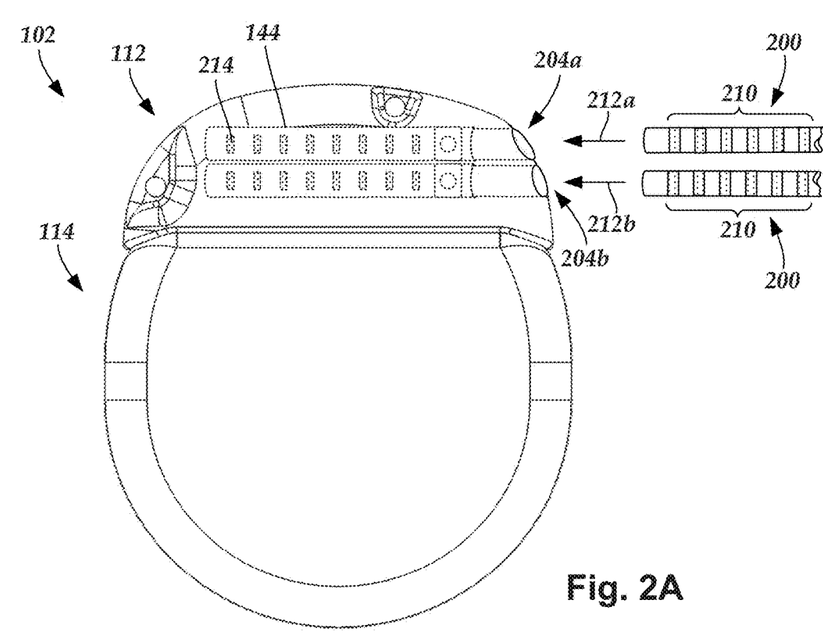
FIG. 2A is a schematic side view of one embodiment of the control module of FIG. 1 configured and arranged to electrically couple to an elongated device, according to the invention.
Figure 2B:
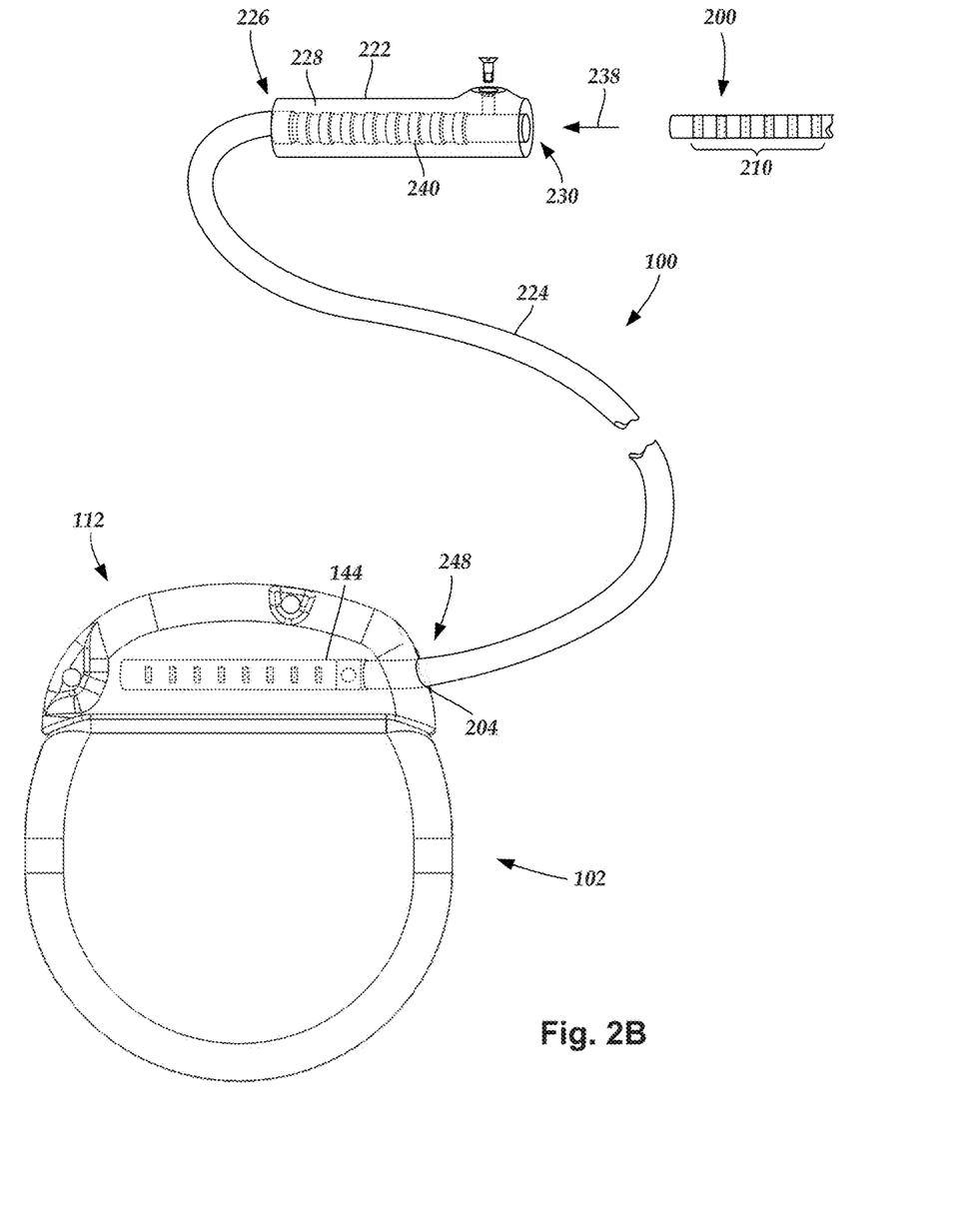
FIG. 2B is a schematic side view of one embodiment of a lead extension configured and arranged to electrically couple the elongated device of FIG. 2A to the control module of FIG. 1, according to the invention.

Terminals (e.g., 210 in FIGS. 2A-2B) are typically disposed along the proximal end of the one or more lead bodies 106 of the electrical stimulation system 100 (as well as any splitters, lead extensions, adaptors, or the like) for electrical connection to corresponding connector contacts (e.g., 214 in FIGS. 2A-2B). The connector contacts are disposed in connectors (e.g., 144 in FIGS. 1-2B; and 222 FIG. 2B) which, in turn, are disposed on, for example, the control module 102 (or a lead extension, a splitter, an adaptor, or the like). Conductor wires (not shown) extend from the terminals to the electrodes 134. Typically, one or more electrodes 134 are electrically coupled to each terminal. In at least some embodiments, each terminal is only connected to one electrode 134.

The conductor wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors may extend through a lumen. There may also be one or more lumens (not shown) that open at, or near, the proximal end of the one or more lead bodies 106, for example, for inserting a stylet to facilitate placement of the one or more lead bodies 106 within a body of a patient. Additionally, there may also be one or more lumens (not shown) that open at, or near, the distal end of the one or more lead bodies 106, for example, for infusion of drugs or medication into the site of implantation of the one or more lead bodies 106. In at least one embodiment, the one or more lumens may be flushed continually, or on a regular basis, with saline, epidural fluid, or the like. In at least some embodiments, the one or more lumens can be permanently or removably sealable at the distal end.

FIG. 2A is a schematic side view of one embodiment of a proximal end of one or more elongated devices 200 configured and arranged for coupling to one embodiment of the control module connector 144. The one or more elongated devices may include, for example, one or more of the lead bodies 106 of FIG. 1, one or more intermediate devices (e.g., a splitter, the lead extension 224 of FIG. 2B, an adaptor, or the like or combinations thereof), or a combination thereof.

The control module connector 144 defines at least one port into which a proximal end of the elongated device 200 can be inserted, as shown by directional arrows 212a and 212b. In FIG. 2A (and in other figures), the connector housing 112 is shown having two ports 204a and 204b. The connector housing 112 can define any suitable number of ports including, for example, one, two, three, four, five, six, seven, eight, or more ports.

The control module connector 144 also includes a plurality of connector contacts, such as connector contact 214, disposed within each port 204a and 204b. When the elongated device 200 is inserted into the ports 204a and 204b, the connector contacts 214 can be aligned with a plurality of terminals 210 disposed along the proximal end(s) of the elongated device(s) 200 to electrically couple the control module 102 to the electrodes (134 of FIG. 1) disposed on the paddle body 104 of the lead 103. Examples of connectors in control modules are found in, for example, U.S. Pat. No. 7,244,150 and U.S. patent application Ser. No. 11/532,844, which are incorporated by reference.

FIG. 2B is a schematic side view of another embodiment of the electrical stimulation system 100. The electrical stimulation system 100 includes a lead extension 224 that is configured and arranged to couple one or more elongated devices 200 (e.g., one of the lead bodies 106 of FIG. 1, a splitter, an adaptor, another lead extension, or the like or combinations thereof) to the control module 102. In FIG. 2B, the lead extension 224 is shown coupled to a single port 204 defined in the control module connector 144. Additionally, the lead extension 224 is shown configured and arranged to couple to a single elongated device 200. In alternate embodiments, the lead extension 224 is configured and arranged to couple to multiple ports 204 defined in the control module connector 144 (e.g., the ports 204*a* and 204*b* of FIG. 1), or to receive multiple elongated devices 200 (e.g., both of the lead bodies 106 of FIG. 1), or both.

A lead extension connector 222 is disposed on the lead extension 224. In FIG. 2B, the lead extension connector 222 is shown disposed at a distal end 226 of the lead extension 224. The lead extension connector 222 includes a connector housing 228. The connector housing 228 defines at least one port 230 into which terminals 210 of the elongated device 200 can be inserted, as shown by directional arrow 238. The connector housing 228 also includes a plurality of connector contacts, such as connector contact 240. When the elongated device 200 is inserted into the port 230, the connector contacts 240 disposed in the connector housing 228 can be aligned with the terminals 210 of the elongated device 200 to electrically couple the lead extension 224 to the electrodes (134 of FIG. 1) disposed along the lead (103 in FIG. 1).

In at least some embodiments, the proximal end of the lead extension 224 is similarly configured and arranged as a proximal end of the lead 103 (or other elongated device 200). The lead extension 224 may include a plurality of conductive wires (not shown) that electrically couple the connector contacts 240 to a proximal end 248 of the lead extension 224 that is opposite to the distal end 226. In at least some embodiments, the conductive wires disposed in the lead extension 224 can be electrically coupled to a plurality of terminals (not shown) disposed along the proximal end 248 of the lead extension 224. In at least some embodiments, the proximal end 248 of the lead extension 224 is configured and arranged for insertion into a connector disposed in another lead extension (or another intermediate device). In other embodiments (and as shown in FIG. 2B), the proximal end 248 of the lead extension 224 is configured and arranged for insertion into the control module connector 144.

Conventionally, many paddle leads are implanted during a laminectomy procedure using forceps to guide and place the paddle body within the epidural space. The paddle body is often difficult to steer using forceps and some surgeons assert that there is a dorsal medial band within the epidural space which can cause problems when inserting the paddle lead. There may also be bumps or other obstacles with in the epidural space which the paddle body must be steered around.

A specific insertion tool can be used to facilitate implantation of a paddle body at a target implantation site within a patient. Advancing the paddle body to the target stimulation location may involve passing one or more obstructions and, in the case of spinal cord stimulation, centering the paddle body along the center line of the spinal cord. As herein described, insertion tools are described that facilitate insertion of a paddle lead into a patient. The insertion tools may have one or more advantages over forceps including, for example, the ability to center the paddle on the spinal cord, increased pushability, the ability to clear obstructions, or entry into the epidural space parallel to the dura, or any combination thereof.

Figure 3A:
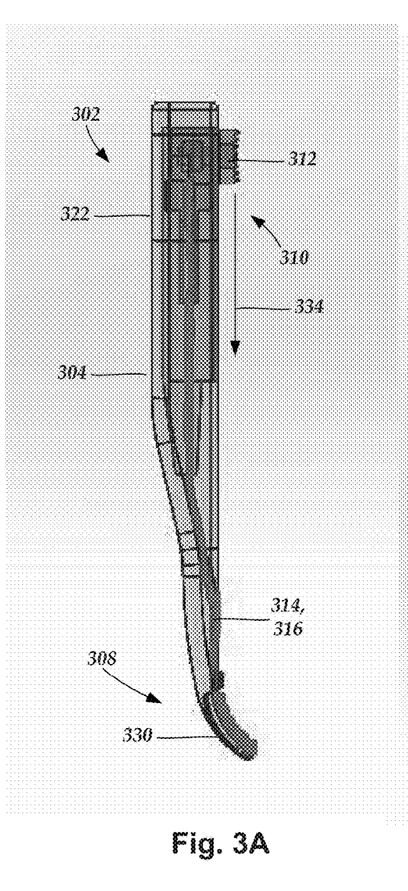
FIG. 3A is a schematic side view of one embodiment of an insertion tool in an insertion position for guiding a paddle lead to a target implantation site within a patient, according to the invention.
Figure 3B:
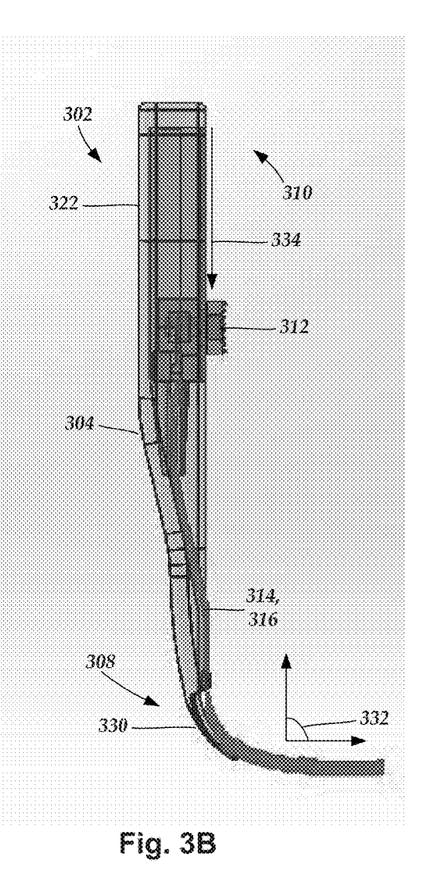
FIG. 3B is a schematic side view of the insertion tool of FIG. 3A in a delivery position, according to the invention.
Figure 3C:
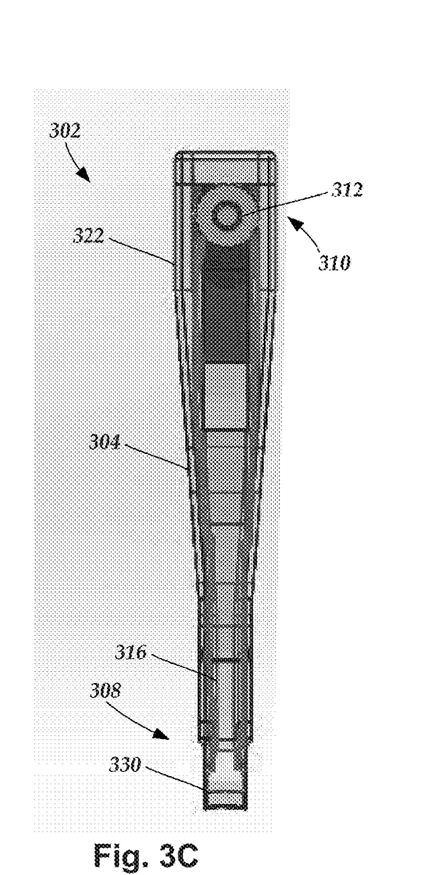
FIG. 3C is a schematic front view of the insertion tool of FIG. 3A, according to the invention.
Figure 3D:
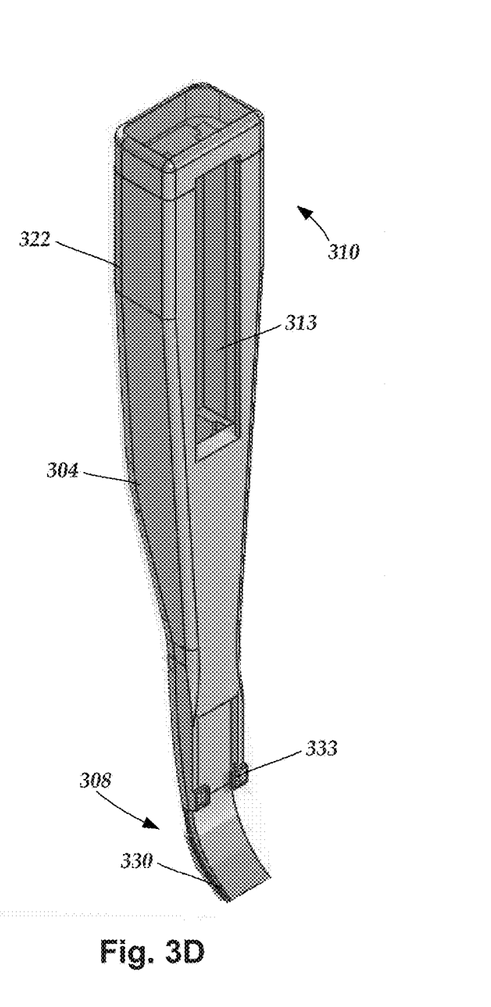
FIG. 3D is a schematic perspective view of an insertion tool body of the insertion tool of FIG. 3A, according to the invention.

FIGS. 3A-3C illustrate one embodiment of an insertion tool 302 for guiding a paddle lead (see e.g., paddle lead 103 of FIG. 1) into a target stimulation location within a patient. The insertion tool 302 includes an insertion tool body 304; a slider 312; a center push piece 314 (see, FIGS. 4A-4D); and extenders 316 (see, FIGS. 4A-4D). The insertion tool body includes a delivery end portion 308, a delivery end portion 310, and a slider slit 313 (FIG. 3D). FIG. 3D illustrates the insertion tool body 304.

The insertion tool body 304 may have any suitable cross-section including, for example, a rectangular, round, or oval-shaped cross-section. In at least some embodiments, the cross-sectional shape of the insertion tool body 304 may change along the longitudinal length of the insertion tool body 304. In at least some embodiments, the delivery end portion 310 of the insertion lead body 304 is wider than the receiving end portion 308 of the insertion tool body 304. It may be advantageous to design the insertion tool body 304 such that the delivery end portion 310 is wider than the receiving end portion 308 because a larger delivery end portion 310 may facilitate gripping of the insertion tool 302 by an operator, while a smaller receiving end portion 308 may facilitate insertion of the insertion tool 302 into the patient's body.

In at least some embodiments, the insertion tool body may be manufactured as an integrated structure (e.g., formed as a one-piece structure). In other embodiments, the insertion tool body 304 may be formed from multiple pieces that are coupled together during manufacture or by the user or any combination thereof. For example, insertion tool or the handling portion 310 of the insertion tool may be formed from two halves that are coupled together. In some embodiments, the receiving end portion 308 is made of a material such as silicone and has an end that is shaped (for example, shaped like an accordion) to fit into an end of the handling portion 310 during assembly of the insertion tool.

Optionally, the delivery end portion 310 may include an insertion tool handle 322, dimensioned and sized to fit ergonomically within the hands of a user of the insertion tool 302. For example, a cross-sectional profile of the delivery end portion 310 may be substantially rectangular with smoothed edges at the corners, making the insertion tool body 304 ergonomic and comfortable to store, hold, and operate.

The delivery end portion 308 includes a curved delivery ramp 330 which reduces the angle of entry of the paddle body relative to the implantation site as the paddle body is extended from the insertion tool 302 into tissue at the desired implantation site. This lower angle of entry can relieve the force exerted by the paddle body on the tissue (for example, the dura if the paddle body is inserted into the spinal cord). In at least some embodiments, the curved delivery ramp 330 is arranged so that the paddle body is inserted at an angle 332 (FIG. 3B) of at least 70, 80, 85, 88, 89, or 90 degrees with respect to the direction 334 of travel of the slider 312. In at least some embodiments, this angle 332 is no more than 110, 105, 100, 95, 98, 99, or 90 degrees. In at least some embodiments, such as for insertion in the epidural space of the spinal cord, the curved delivery ramp 330 is inserted into an entrance hole created by a laminectomy and the paddle body is directed by the curved delivery ramp to enter the epidural space parallel to the dura. In this manner, the insertion tool 302 can be held at or near (e.g., within 1, 2, 5, or 10 degrees of) a 90 degree angle with respect to the desired final paddle body placement position which is often preferable to the surgeon during the insertion procedure. In at least some embodiments, the insertion tool 302 can include one or more retainers 333 (FIG. 3D) that extend from a side of the insertion tool and partially over the paddle body to retain the paddle body within the insertion tool during insertion into the patient.

The extenders 316 and center push piece 314 are coupled to the slider 312. The slider 312 moves along the slider slit 313 between an insertion position, illustrated in FIGS. 3A, 4A and 4B, to a delivery position, illustrated FIGS. 3B, 4C, and 4D. The insertion position can be used for insertion of the tool into the patient and the delivery position, with the center push piece 314, extenders 316, and paddle body extended, is for extending the paddle body away from the insertion tool 302 for delivery of the paddle body to the desired implantation site. The extenders 316 and center push piece 314 are curved along their distal end to facilitate delivery of the paddle body along the curved delivery ramp 330. In at least some embodiments, as described in more detail below, when the slider 312 is retracted from the delivery position to the insertion position, the extenders 316 may be retracted first leaving the center push piece 314 in place to prevent or reduce any retraction of the paddle body with the extenders.

Figure 4A:
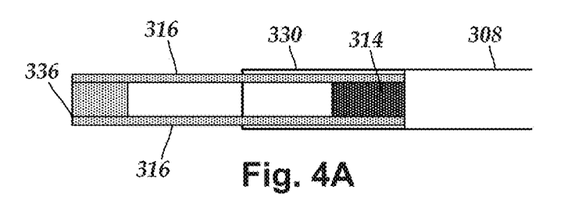
FIG. 4A is a schematic top view of one embodiment of a delivery end portion of the insertion tool of FIG. 3A, according to the invention.

FIGS. 4A-4D illustrate the delivery end portion 308 and other components of the insertion tool 302 at various stages during at least some embodiments of an insertion procedure. FIG. 4A illustrates the delivery end portion 308 with curved delivery ramp 330 and the distal ends of the extenders 316 and center push piece 314 prior to loading a paddle lead. In at least some embodiments, the distal ends of the extenders 316 are coupled together by a crosspiece 336.

Figure 4B:
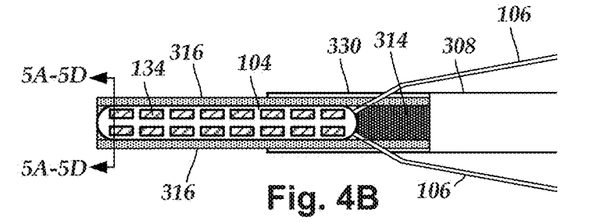
FIG. 4B is a schematic top view of one embodiment of the portion of the paddle lead and the portion of the insertion tool of FIG. 4A in the insertion position, according to the invention.
Figure 5A:
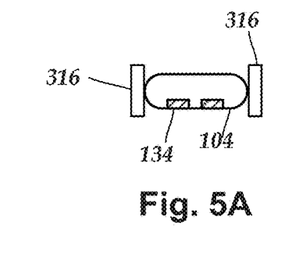
FIG. 5A is a schematic cross-sectional view of one embodiment of a paddle body and extenders, according to the invention.
Figure 5B:
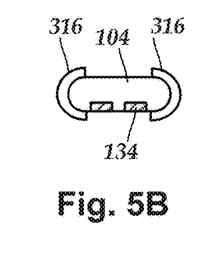
FIG. 5B is a schematic cross-sectional view of a second embodiment of a paddle body and extenders, according to the invention.
Figure 5C:
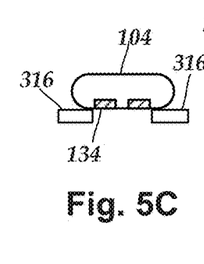
FIG. 5C is a schematic cross-sectional view of a third embodiment of a paddle body and extenders, according to the invention.
Figure 5D:
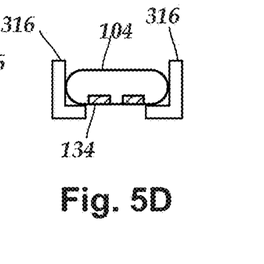
FIG. 5D is a schematic cross-sectional view of a fourth embodiment of a paddle body and extenders, according to the invention.

FIG. 4B illustrates the delivery end portion 308 with a paddle body 104, containing electrodes 134 and coupled to lead bodies 106, disposed on or between the extenders 316 with the slider 312 in the insertion position (FIG. 3A). The crosspiece 336 may provide a platform for a portion of the paddle body 104. The extenders 316 may be disposed beneath or to the side (or both beneath and to the side) of the paddle body. FIGS. 5A-5D illustrate, in cross-section, four different embodiments of the extenders 316 and the paddle body 104. In FIG. 5A, the paddle body 104 is disposed between parallel extenders 316 which each include a vertical rail. In FIG. 5B, the extenders 316 are shaped to fit around the paddle body 104 and extend over portions of the top and bottom surfaces of the paddle body and form curved rails. In FIG. 5C, the extenders 316 are disposed below the paddle body 104 and each form a horizontal platform. In FIG. 5D, the extenders 316 are disposed below and to the side of the paddle body 104 and each form a vertical rail and horizontal platform. It will be understood that other extender shapes can be employed include other embodiments with a vertical rail, horizontal platform, curved rail, or any combination thereof. Preferably, the distal end of the extenders 316 and crosspiece 336 allows for the paddle body 104 to slide off as the extenders 316 and crosspiece are retracted.

Figure 4C:
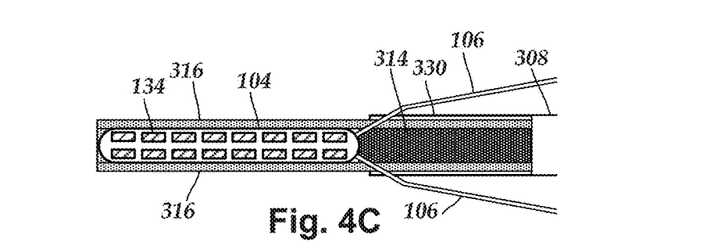
FIG. 4C is a schematic top view of one embodiment of the portion of the paddle lead and the portion of the insertion tool of FIG. 4B in the delivery position, according to the invention.
Figure 4D:
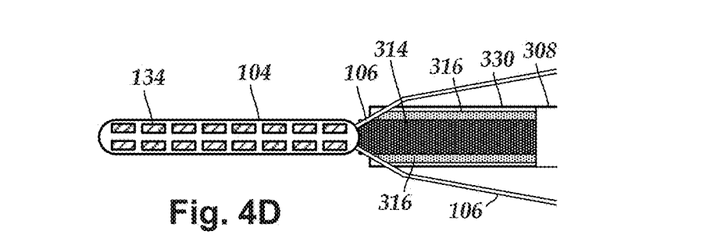
FIG. 4D is a schematic top view of one embodiment of the portion of the paddle lead and the portion of the insertion tool of FIG. 4C with the extenders retracted after entering the delivery position, according to the invention.

During insertion of the insertion tool or when the insertion tool is fully inserted, the slider 312 can be advanced to the delivery position (FIG. 3B) in which the extenders 316 and center push piece 314 are pushed forward carrying the paddle body 104, as illustrated in FIG. 4C. The extenders 316 are then retracted, using the slider 312, leaving the paddle body 104 in place, as illustrated in FIG. 4D. In at least some embodiments, the center push piece 314 remains in place as the extenders 316 are retracted to prevent or reduce retraction of the paddle body 103 with the extenders 103, as illustrated in FIG. 4D. The insertion tool 302 can then be removed leaving the paddle body 103 implanted within the patient.

In a method of implanting a paddle lead, the user inserts the paddle body into the tip of the insertion tool. The lead body or lead bodies extend away from the paddle body. The insertion tool is place with the tip of the tool at, or near, the desired implantation site (for example, an entrance to the epidural space). The contour of the curved delivery ramp can be aligned with the desired implantation site (for example, aligned with the curvature of the spinal canal). The user slides the slider forward to advance the paddle body and extenders to the implantation site (for example, into the epidural space parallel to the dura). The user can angle the insertion tool to steer the tip of the paddle body. When the paddle body is implanted at the desired site (which may optionally be determined using any suitable imaging technique), the slider can be slid backwards to retract the extenders leaving the paddle body in place (optionally, facilitated by leaving the center push piece in place against the paddle body). The tool can then be removed.

Figure 6A:
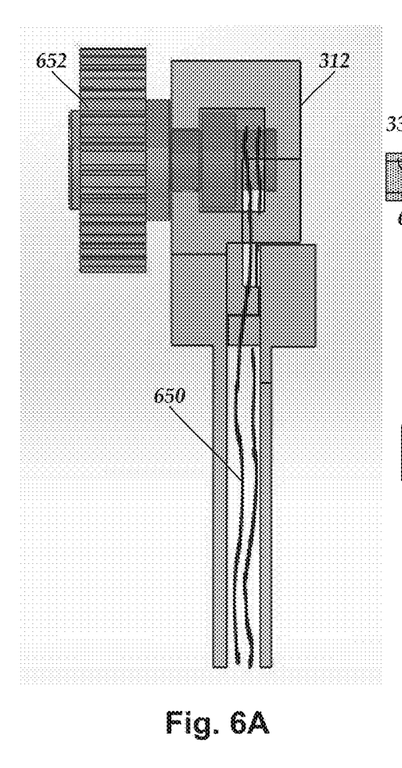
FIG. 6A is a schematic side view of one embodiment of a slider and cabling for use an insertion position for guiding a paddle lead to a target implantation site within a patient, according to the invention.
Figure 6B:
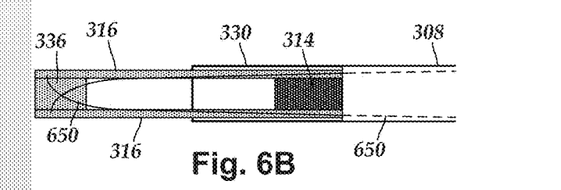
FIG. 6B is a schematic top view of one embodiment of the portion of the paddle lead and the portion of the insertion tool of FIG. 6A in the insertion position, according to the invention.
Figure 6C:
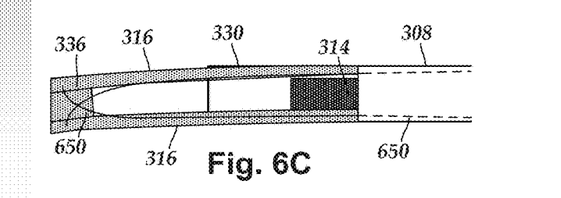
FIG. 6C is a schematic top view of one embodiment of the portion of the paddle lead and the portion of the insertion tool of FIG. 6B in the insertion position with the cabling used to steer the tip of the insertion tool, according to the invention.

In some embodiments, the insertion tool includes additional features that can provide increased steerability of the paddle body. FIGS. 6A-6C illustrate portions of an insertion tool that includes such features. This insertion tool includes the same elements as insertion tool 302 described above as well as additional elements described herein. FIG. 6A illustrates cabling 650 (for example, two or more cables, as illustrated in FIG. 6A) that is attached to the slider 312 and a slider wheel 652 that can rotate (or otherwise be manipulated) to adjust the cabling 650. The cabling can be attached to the slider directly or by wrapping a portion of the cabling around the slider. FIG. 6B illustrates the delivery end portion 308 with extenders 316, center push piece 314, and crosspiece 336. The cabling 650 is attached to the ends of the two extenders 316 (or to portions of the crosspiece 336), as illustrated in FIG. 6B. In the illustrated embodiments, the two cables of the cabling 650 cross to provide a larger turn radius than could be achieved if the cables did not cross. It will be understood, however, that other embodiments of the insertion tool can include uncrossed cables. By rotating the slider wheel 652, the cabling 650 to one extender 316 is shortened and the cabling to the other extender is lengthened resulting in a pull to one side or the other, depending on the direction of rotation of the slider wheel 652, as illustrated in FIG. 6C.

Figure 7:
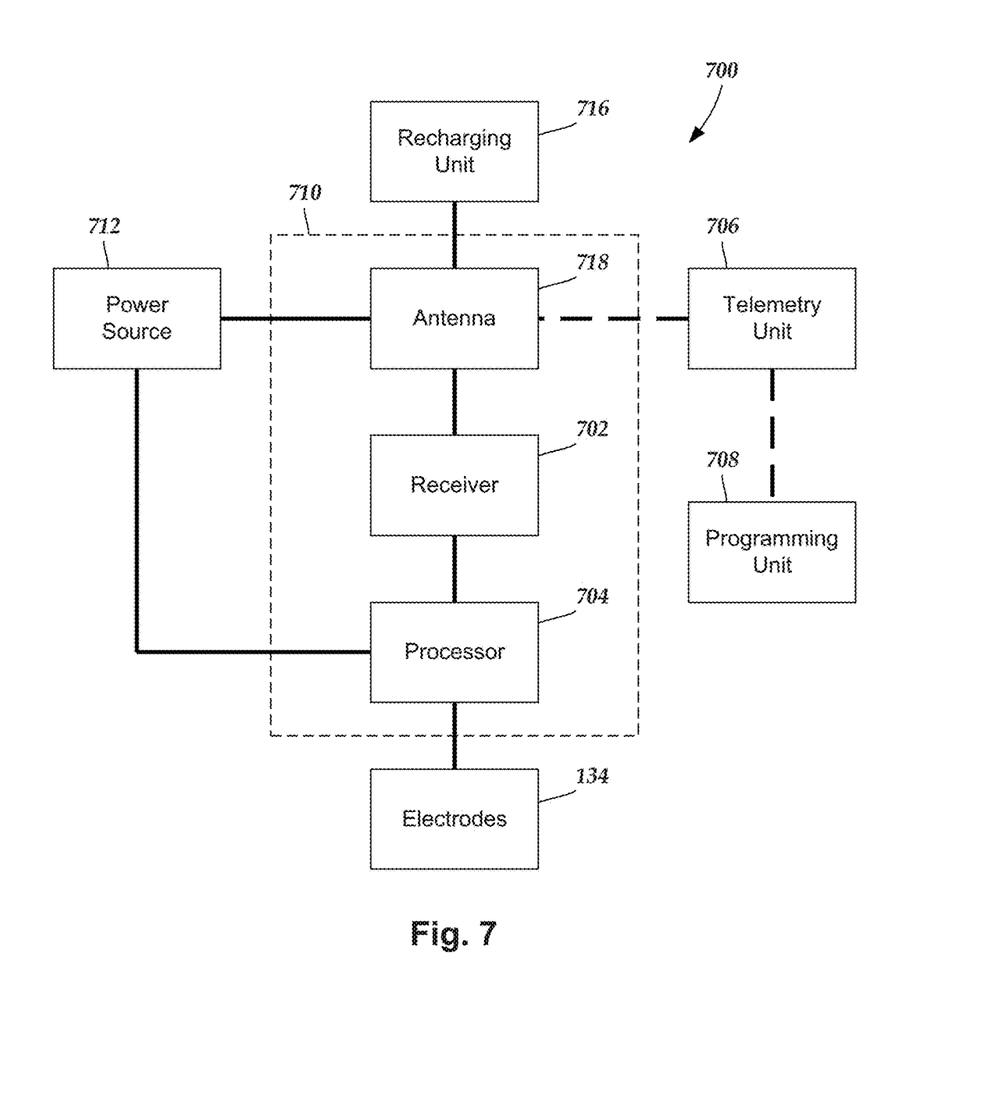
FIG. 7 is a schematic overview of one embodiment of components of a stimulation system, including an electronic subassembly disposed within a control module, according to the invention.

FIG. 7 is a schematic overview of one embodiment of components of an electrical stimulation system 700 including an electronic subassembly 710 disposed within a control module. It will be understood that the electrical stimulation system can include more, fewer, or different components and can have a variety of different configurations including those configurations disclosed in the stimulator references cited herein.

Some of the components (for example, power source 712, antenna 718, receiver 702, and processor 704) of the electrical stimulation system can be positioned on one or more circuit boards or similar carriers within a sealed housing of an implantable pulse generator, if desired. Any power source 712 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 718 or a secondary antenna. The external power source can be in a device that is mounted on the skin of the user or in a unit that is provided near the user on a permanent or periodic basis.

If the power source 712 is a rechargeable battery, the battery may be recharged using the optional antenna 718, if desired. Power can be provided to the battery for recharging by inductively coupling the battery through the antenna to a recharging unit 716 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 704 is generally included to control the timing and electrical characteristics of the electrical stimulation system. For example, the processor 704 can, if desired, control one or more of the timing, frequency, strength, duration, and waveform of the pulses. In addition, the processor 704 can select which electrodes can be used to provide stimulation, if desired. In some embodiments, the processor 704 may select which electrode(s) are cathodes and which electrode(s) are anodes. In some embodiments, the processor 704 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 708 that, for example, allows modification of pulse characteristics. In the illustrated embodiment, the processor 704 is coupled to a receiver 702 which, in turn, is coupled to the optional antenna 718. This allows the processor 704 to receive instructions from an external source to, for example, direct the pulse characteristics and the selection of electrodes, if desired.

In one embodiment, the antenna 718 is capable of receiving signals (e.g., RF signals) from an external telemetry unit 706 which is programmed by a programming unit 708. The programming unit 708 can be external to, or part of, the telemetry unit 706. The telemetry unit 706 can be a device that is worn on the skin of the user or can be carried by the user and can have a form similar to a pager, cellular phone, or remote control, if desired. As another alternative, the telemetry unit 706 may not be worn or carried by the user but may only be available at a home station or at a clinician's office. The programming unit 708 can be any unit that can provide information to the telemetry unit 706 for transmission to the electrical stimulation system 700. The programming unit 708 can be part of the telemetry unit 706 or can provide signals or information to the telemetry unit 706 via a wireless or wired connection. One example of a suitable programming unit is a computer operated by the user or clinician to send signals to the telemetry unit 706.

The signals sent to the processor 704 via the antenna 718 and receiver 702 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 700 to cease operation, to start operation, to start charging the battery, or to stop charging the battery.

In other embodiments, the stimulation system does not include an antenna 718 or receiver 702 and the processor 704 operates as programmed.

Optionally, the electrical stimulation system 700 may include a transmitter (not shown) coupled to the processor 704 and the antenna 718 for transmitting signals back to the telemetry unit 706 or another unit capable of receiving the signals. For example, the electrical stimulation system 700 may transmit signals indicating whether the electrical stimulation system 700 is operating properly or not or indicating when the battery needs to be charged or the level of charge remaining in the battery. The processor 704 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A paddle lead insertion tool, comprising:
   an insertion tool body comprising a delivery end portion and a slider slit;
   a slider comprising a portion disposed within the slider slit;
   a plurality of extenders coupled to the slider and each of the extenders extending to the delivery end portion and configured and arranged to receive a paddle body of a paddle lead between the extenders or upon the extenders; and
   a center push piece coupled to the slider and disposed between the extenders and configured and arranged to directly engage and directly push against a proximal end of the paddle body of the paddle lead;
   wherein the slider is configured and arranged to move between an insertion position and a delivery position, wherein the insertion tool is configured and arranged to extend the extenders and center push piece when the slider moves from the insertion position to the delivery position to extend the paddle body received by the insertion tool, wherein the insertion tool is further configured and arranged to retract the extenders without retracting the center push piece when the slider moves from the delivery position towards the insertion position.

2. The insertion tool of claim 1, wherein the extenders each comprise a vertical or curved rail configured and arranged to be disposed adjacent sides of the paddle body.

3. The insertion tool of claim 1, wherein the extenders each comprise a horizontal platform configured and arranged to be at least partially disposed beneath a portion of the paddle body.

4. The insertion tool of claim 1, further comprising a crosspiece coupling ends of the extenders.

5. The insertion tool of claim 1, further comprising cabling coupled to the slider and to distal end portions of the extenders and configured and arranged to cooperate with the slider and the extenders for steering the paddle body.

6. The insertion tool of claim 5, wherein the slider comprises a rotatable slider wheel coupled to the cabling and configured and arranged to rotate and pull the distal end portion of one of the extenders for steering the paddle body.

7. The insertion tool of claim 1, wherein the slider is configured and arranged to move along a first direction between the insertion position and the delivery position, wherein the delivery end portion of the insertion tool body comprises a curved delivery ramp configured and arranged to deliver the paddle body received by the insertion tool at an angle, defined between the paddle body and the first direction, in a range of 80 to 100 degrees.

8. The insertion tool of claim 7, wherein the angle is in a range from 85 to 95 degrees.

9. An insertion kit, comprising:
the insertion tool of claim 1; and
a paddle lead comprising a paddle body, at least one lead body extending from the paddle body, a plurality of electrodes disposed on the paddle body, and a plurality of terminals disposed along the at least one lead body and electrically coupled to the electrodes.

10. A method of implanting a paddle lead, the method comprising:
disposing a paddle body of the paddle lead between or upon the extenders of the insertion tool of claim 1;
inserting the insertion tool and paddle body into the patient;
advancing the slider to the delivery position to extend the extenders, the center push piece, and the paddle body toward an implantation site within the patient;
retracting the slider to retract the extenders without retracting the center push piece to deliver the paddle body at the implantation site; and
removing the insertion tool leaving the paddle body at the implantation site.

11. A paddle lead insertion tool, comprising:
an insertion tool body comprising a delivery end portion and a slider slit;
a slider comprising a portion disposed within the slider slit and configured and arranged to move along a first direction between an insertion position and a delivery position, wherein the delivery end portion of the insertion tool body comprises a curved delivery ramp configured and arranged to deliver a paddle body of a paddle lead received by the insertion tool at an angle, defined between the paddle body and the first direction, in a range of 70 to 260 degrees; and
two extenders coupled to the slider and each of the two extenders extending to the delivery end portion and configured and arranged to receive the paddle body of the paddle lead between the two extenders with the two extenders disposed opposite each other along opposing sides of the paddle body;
wherein the slider is configured and arranged to move between an insertion position and a delivery position, wherein the insertion tool is configured and arranged to extend the extenders when the slider moves from the insertion position to the delivery position to extend the paddle body received by the insertion tool, wherein the insertion tool is configured and arranged to retract the extenders when the slider moves from the delivery position towards the insertion position.

12. The insertion tool of claim 11, further comprising a center push piece coupled to the slider and disposed between the extenders and configured and arranged to directly engage and directly push against a proximal end of the paddle body of the paddle lead, wherein the insertion tool is configured and arranged to extend the extenders and center push piece when the slider moves from the insertion position to the delivery position to extend the paddle body received by the insertion tool, wherein the insertion tool is further configured and arranged to retract the extenders without retracting the center push piece when the slider moves from the delivery position towards the insertion position.

13. The insertion tool of claim 11, wherein the angle is in a range from 80 to 100 degrees.

14. The insertion tool of claim 11, wherein the angle is in a range from 85 to 95 degrees.

15. The insertion tool of claim 11, further comprising cabling coupled to the slider and to distal end portions of the extenders and configured and arranged to cooperate with the slider and the extenders for steering the paddle body.

16. The insertion tool of claim 5, wherein the slider comprises a rotatable slider wheel coupled to the cabling and configured and arranged to rotate and pull the distal end portion of one of the extenders for steering the paddle body.

17. The insertion tool of claim 11, wherein the extenders each comprise a vertical or curved rail configured and arranged to be disposed adjacent the opposing sides of the paddle body.

18. The insertion tool of claim 11, wherein the extenders each comprise a horizontal platform configured and arranged to be at least partially disposed beneath a portion of the paddle body.

19. An insertion kit, comprising:
the insertion tool of claim 11; and
a paddle lead comprising a paddle body, at least one lead body extending from the paddle body, a plurality of electrodes disposed on the paddle body, and a plurality of terminals disposed along the at least one lead body and electrically coupled to the electrodes.

20. A method of implanting a paddle lead, the method comprising:
disposing a paddle body of the paddle lead between or upon the extenders of the insertion tool of claim 11;
inserting the insertion tool and paddle body into the patient;
advancing the slider to the delivery position to extend the extenders and the paddle body toward an implantation site within the patient;
retracting the slider to retract the extenders to deliver the paddle body at the implantation site; and
removing the insertion tool leaving the paddle body at the implantation site.

* * * * *